United States Patent [19]

Allen, Jr. et al.

[11] Patent Number: 5,522,810
[45] Date of Patent: Jun. 4, 1996

[54] COMPRESSIVELY RESISTANT AND RESILIENT FIBROUS NONWOVEN WEB

[75] Inventors: Roe C. Allen, Jr., Roswell; Andrew S. Burnes, Lawrenceville, both of Ga.

[73] Assignee: Kimberly-Clark Corporation, Neenah, Wis.

[21] Appl. No.: 463,593

[22] Filed: Jun. 5, 1995

[51] Int. Cl.$^6$ .............................. A61F 13/15; A61F 13/20
[52] U.S. Cl. ......................... 604/366; 604/358; 604/370; 428/373; 428/374
[58] Field of Search ........................... 604/358, 365–367, 604/370; 428/224, 373, 374

[56] References Cited

U.S. PATENT DOCUMENTS

| | | |
|---|---|---|
| 3,276,944 | 10/1966 | Levy . |
| 3,338,922 | 8/1967 | Kinney . |
| 3,341,394 | 9/1967 | Kinney . |
| 3,502,538 | 3/1970 | Petersen . |
| 3,502,763 | 3/1970 | Hartmann . |
| 3,542,615 | 11/1970 | Dobo et al. . |
| 3,692,618 | 9/1972 | Dorschner et al. . |
| 3,802,817 | 4/1974 | Matsuki et al. . |
| 4,340,563 | 7/1982 | Appel et al. . |
| 4,798,603 | 1/1989 | Meyer et al. . |
| 5,137,600 | 8/1992 | Barnes et al. ............. 428/311.1 |
| 5,143,779 | 9/1992 | Newkirk et al. ............. 428/218 |
| 5,294,478 | 3/1994 | Wanek et al. . |
| 5,364,382 | 11/1994 | Latimer et al. . |
| 5,382,400 | 1/1995 | Pike et al. . |

FOREIGN PATENT DOCUMENTS

803714   1/1969   Canada .

*Primary Examiner*—John G. Weiss
*Assistant Examiner*—P. Zuttarelli
*Attorney, Agent, or Firm*—Patrick C. Wilson; Nicholas N. Leach

[57] ABSTRACT

Disclosed herein is a compressively resistant and resilient fibrous nonwoven web which is suitable for a wide variety of uses including, but not limited to, a portion of a personal care absorbent product which is located on the side of the absorbent core of the product which faces the wearer. The nonwoven web can include bicomponent fiber and has a thickness of 2.5 mm or greater at a pressure of 68.9 pascal, a specific volume of 14 cc/g or greater at a pressure of 6,895 pascal, and a Frazier air permeability of 100 cubic meters per square meter per minute or greater.

31 Claims, 1 Drawing Sheet

COMPRESSIVELY RESISTANT AND RESILIENT FIBROUS NONWOVEN WEB

FIELD OF THE INVENTION

The present invention is related to fibrous nonwoven webs which are useful in, among other things, personal care absorbent products. More particularly, the present invention relates to lofty fibrous nonwoven webs which due to their unique design parameters, are compression resistant and resilient. As a result, the fibrous nonwoven webs according to the present invention have particular use as separation layers in personal care absorbent products to keep the liquid filled absorbent cores of such products away from the wearer's skin.

BACKGROUND OF THE INVENTION

The present invention is directed to a compressively resistant and resilient fibrous nonwoven web which is suitable for a number of uses including, but not limited to, personal care absorbent articles. Other uses for the material of the present invention are also contemplated to be within the scope of the present invention.

Personal care absorbent products such as diapers, training pants, incontinence devices, feminine hygiene products, bandages and the like are designed to absorb body fluids including blood, urine, menses and feces. In certain instances these products must be able to quickly absorb relatively large quantities of liquid, urine being an example, and still keep the wearer as dry and comfortable as possible. Typically, such personal care absorbent products will include a liquid permeable top sheet, a bottom sheet and an absorbent core disposed between the top sheet and the bottom sheet. The top sheet is usually made from some type of fibrous permeable nonwoven web such as a bonded carded web or a spunbonded web. The bottom sheet will typically be made from some type of material or laminate which is liquid impervious, and optionally, breathable.

The absorbent core is usually made from wood pulp fibers also referred to as "fluff" and can optionally include superabsorbent particles which are designed to absorb many times their own weight in liquid. When a child or adult urinates, the urine passes through the top sheet and is absorbed into the absorbent core below. A problem with the absorbent cores is that they are not very effective at quickly channeling liquid away to more remote parts of the absorbent structure. As a result, at least a part of the liquid retained in the crotch area may wick back to the top sheet which is usually in contact with the wearer's skin. This urine-soaked material is at the very least uncomfortable, inhibits air flow to the skin and may possibly exacerbate any skin conditions which are present.

Attempts have been made to alleviate these problems by placing additional materials in between the top sheet and the absorbent core. These materials have been referred to as transfer layers whose function it is to take up the liquid delivered to it through the top sheet and then transfer it to the absorbent core. One such material is currently used by the assignee of record in its Huggies® Ultratrim and Supreme diapers. The transfer layer consists of a 50 gram per square meter through air thermally bonded carded web made from a weight percent blend of 60 percent 6 denier polyester staple fibers and 40 percent polyethylene sheath/polypropylene core 3 denier bicomponent fibers. The resultant web has a thickness of 80 mils (2.03 millimeters). While this material has helped in reducing wetness against the skin, improvements are still desirable.

Ideally, such a transfer layer would readily take in liquid to get it away from the skin. It would give up the same liquid to other components in the diaper or other personal care absorbent product so that it would not stay wet and it also would be able to separate the skin and top sheet from the rest of the absorbent system. Lastly, the material would be able to maintain the separation under a variety of conditions.

Current transfer layers are able to take in fluids to get them away from the skin and then pass them away to the absorbent core. A problem they have however is that they are not effective at maintaining separation during heavy compression cycles such as when a baby or adult is sitting or sleeping. There is therefore a need for a compressively resistant and resilient material which will adequately separate the wearer from the fluid laden absorbent core. A supposed solution would simply be to "beef-up" the existing materials to achieve these objectives. However, simply increasing basis weight can adversely impact the ability of the material to take in fluids and then readily give them up the absorbent core. In addition, if the material becomes too thick, it will make the end product too big and bulky especially when considering the small dimensions of a baby in the perineal area of the torso. Consequently, these properties must be combined and optimized preferably in a single material. The present invention is directed to such a material as will become more apparent from the following description, drawings and claims.

SUMMARY OF THE INVENTION

The present invention is directed to a compressively resistant and resilient fibrous nonwoven web which is suitable for a number of uses including components in personal care absorbent products such as a diapers, training pants, feminine hygiene products, incontinence devices, bandages and the like. All of these products typically include a liquid permeable top sheet or body side liner, an outer cover or bottom sheet and an absorbent core disposed between the top sheet and the bottom sheet. Additionally these products may include a separation layer disposed between the top sheet and the absorbent core. The material of the present invention may be used as all or a portion of the top sheet, separation layer and/or absorbent core. It includes a plurality of randomly-deposited fibers some or all of which are bonded to one another to form a nonwoven web. The web so formed had a thickness of about 2.5 millimeters or greater at a pressure of 68.9 pascals, a specific volume of 14 cubic centimeters per gram or greater at a pressure of 6,895 pascals, a compression resistance of 25 percent or greater and a compression resiliency of 80 percent or greater. The Frazier air permeability is dependent upon basis weight, density and fiber size of the nonwoven web. For higher basis weight materials in excess of about 50 grams per square meter, the web may have a Frazier air permeability of 100 cubic meters per square meter per minute or greater. In more refined embodiments the fibrous nonwoven web may be made from or include bicomponent fibers which are thermally bonded to one another such as by through air bonding. The resultant material may be used as the top sheet or separation layer in personal care absorbent products including diapers, training pants, incontinence devices, sanitary napkins, bandages and the like.

DETAILED DESCRIPTION OF THE INVENTION

The present invention is directed to a lofty fibrous nonwoven web which, among other things, is particularly well-suited as a means for separating the absorbent core of a personal care absorbent product from the skin of the wearer of such products.

Personal care absorbent products typically include a liquid permeable body side liner and a liquid impermeable backing layer or baffle with an absorbent core disposed therebetween. As discussed in the background, a common problem with many of these products and their designs is that there is insufficient spacing between the absorbent core and the wearer's skin. As a result, even under normal conditions, sufficient pressure can be applied to the overall structure such that the liquid retained in the absorbent core will tend to flow back and contact the wearer's skin. Examples of such personal care absorbent products which can have this problem, include, but are not limited to, sanitary napkins and other feminine hygiene products, diapers, training pants, incontinence garments, bandages and the like. The present invention attempts to reduce this problem by providing a lofty fibrous nonwoven web which is compression resistant and also resilient. By being compression resistant, the material tends to resist compression thereby maintaining a spaced-apart relationship between the absorbent core and the wearer. In addition, the lofty fibrous nonwoven web according to the present invention has a very open structure which promotes air circulation and because of the open structure, will not readily retain fluids. Consequently, the material tends to provide an air cushion between the absorbent core and the wearer. If the material is compressed, due to the nature of its construction, it tends to exhibit compression resilience in that the material will spring back towards its original thickness once the compressive load has been released. This too acts to maintain the open structure of the material thereby maintaining the separation characteristics.

Figure 1:
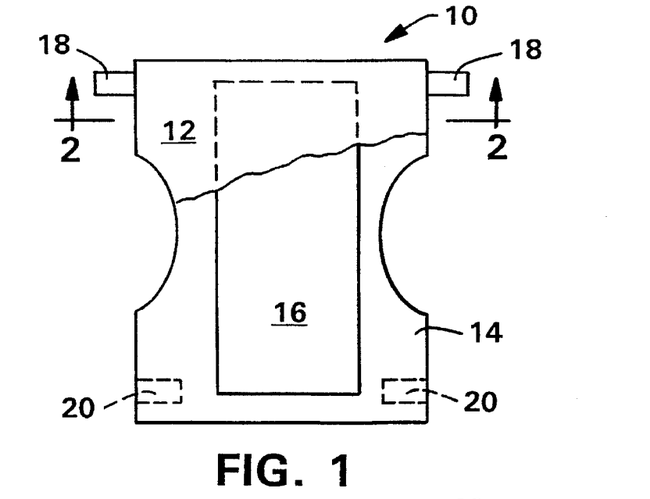
FIG. 1 is a top plan view in partial cut-away of a personal care absorbent product, in this case, a diaper which can utilize the compressively resistant and resilient fibrous nonwoven web according to the present invention.
Figure 2:
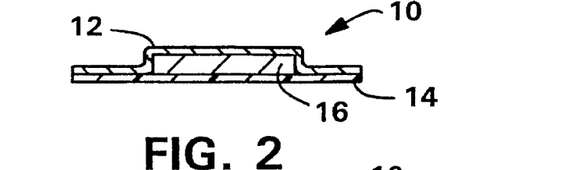
FIG. 2 is a cross-sectional view of FIG. 1 taken along line 2—2 in FIG. 1.

Referring to FIGS. 1 and 2 there is shown a personal care absorbent product, in this case, a diaper 10. The present invention will be described in conjunction with this particular embodiment; however, it should not be interpreted as limiting the scope or application of the present invention. The diaper 10, as with most all personal care absorbent products, includes a liquid permeable top sheet 12, a bottom sheet 14 and an absorbent core 16 disposed between the liquid permeable top sheet 12 and the bottom sheet 14. In addition, many personal care absorbent products such as the diaper 10 will include some type of fastening means 18 to secure the product about the wearer. A further example of such products, their designs and component materials can be found in U.S. Pat. No. 5,364,382 to Latimer et al., U.S. Pat. No. 4,798,603 to Meyer et al. and U.S. Pat. No. 5,294,478 to Wanek et al. all of which are incorporated herein by reference in their entirety.

The top sheet 12 is designed to contact the wearer's skin and, therefore, should be soft to the touch while resisting abrasion. It also should be liquid pervious. Suitable materials for the top sheet 12 include, but are not limited to, a multiplicity of fibrous nonwoven webs such as bonded carded webs and more continuous fiber webs such as spunbond webs. Other suitable materials include liquid pervious films and laminates of films and/or nonwovens.

The bottom sheet 14 can be made from a variety of materials including, but not limited to, plastic films, fibrous nonwoven webs, foams and combinations of the foregoing including laminates. The main attribute of the bottom sheet 14 is that it retain any deposited solids or liquids that are received by the diaper 10. As a result, it is generally desirable that the bottom sheet 14 be liquid impervious. In order to facilitate increased comfort, it also may be desirable to form the bottom sheet 14 such that it is breathable. Some materials such as fibrous nonwoven webs tend to be breathable by nature due to their construction. Other materials such as plastic films can be made breathable by aperturing and/or through the use of microporous films which oftentimes contain fillers. Such filler-containing films are either stretched or crushed to create pores adjacent the filler thereby providing a path through the film which will permit, for example, water vapor to be transmitted therethrough. Other films are available which transmit water vapor using diffusion mechanisms.

The absorbent core 16 is disposed between the top sheet 12 and bottom sheet 14 and is used to absorb the main portion of the body fluids or other liquids delivered to it through the top sheet 12. The absorbent core may be made from a wide variety of materials including, but not limited to, natural and synthetic wood pulp fluff fibers, hydrophilic thermoplastic fibers and/or thermoplastic fibers which have been treated to be hydrophilic. The absorbent core also may contain superabsorbents. Furthermore, these materials may be used alone or in combination. For example, wood pulp fluff may be used alone or in combination with a superabsorbent to increase the overall capacity of the absorbent core. In addition, more rigid thermoplastic fibers may be used to maintain the integrity of the absorbent core and to assist in preventing collapse of the absorbent core once it has become wetted.

The fastening means 18 shown in FIG. 1 can be in the form of adhesive diaper fastening tapes and/or mechanical hook and loop fastener systems. For example, the fastening means 18 can be pieces of hook material which are designed to engage a corresponding loop material 20 such as is shown phantom in FIG. 1 and which is attached to the exterior surface of the bottom sheet 14. Alternatively, if the bottom sheet 14 employs a fibrous nonwoven web on its exterior surface, the hook members of the fastening means 18 may be attached directly to the fibers of the nonwoven web forming the bottom sheet 14.

Figure 3:
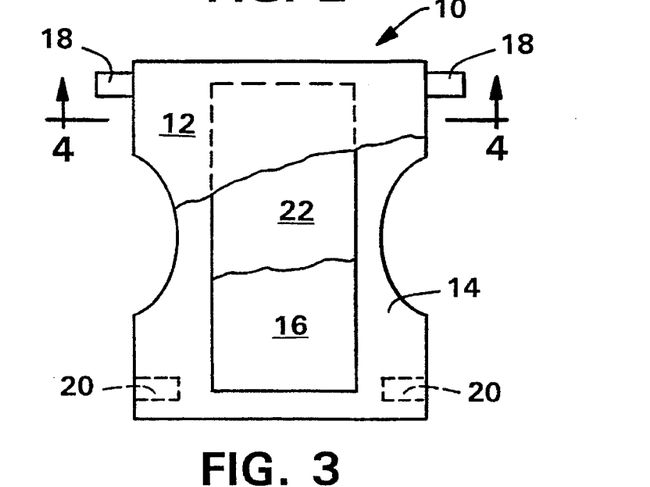
FIG. 3 is a top plan view in partial cut-away of a personal care absorbent product, in this case, a diaper which may also utilize the compressively resistant and resilient fibrous nonwoven web according to the present invention.
Figure 4:
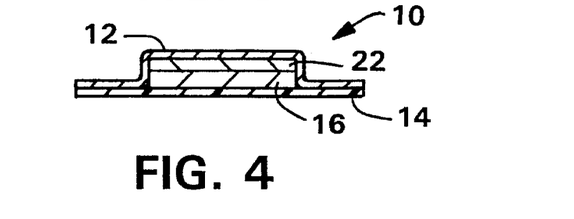
FIG. 4 is a cross-sectional side view of FIG. 3 taken along line 4—4 in FIG. 3.

Referring to FIGS. 3 and 4 there is shown another diaper construction 10. Like reference numerals are used for like elements. In this embodiment the diaper 10 is identical to that shown in FIGS. 1 and 2 except for the incorporation of an additional separation layer 22 between the liquid permeable top sheet 12 and the absorbent core 16. The purpose of the separation layer 22 is to further distance the top sheet 12 from the absorbent core 16 in an effort to reduce liquid flow back from the absorbent core 16 to the top sheet 12. As shown in FIGS. 3 and 4, the separation layer 22 is in vertical juxtaposition with the absorbent core 16 and has the same general length and width dimensions as the absorbent core 16. If desired, the separation layer 22 can be varied in size and thus can be made smaller or larger than the absorbent core 16. In addition, the separation layer 22 can be made to the same dimensions as the liquid permeable top sheet 12 thereby causing it to cover the entire absorbent core 16 and the bottom sheet 14. Generally, the separation layer 22 will be made from a fibrous nonwoven web with a sufficient degree of hydrophilicity so as to allow liquid transport through the structure from the liquid permeable top sheet 12 to the absorbent core 16.

The compressively resistant and resilient fibrous nonwoven web according to the present invention may be used to form either or both the liquid permeable top sheet 12 and the separation layer 22 shown in FIGS. 1 through 4 of the drawings. In some situations, the material according to the present invention may not have as soft a feel as is typically possible with respect to conventional top sheet materials in which case it may be desirable to place the material of the present invention underneath the top sheet 12 such as in the configuration of a separation layer 22. The compressively resistant and resilient fibrous nonwoven web according to the present invention may be used alone or in combination with other materials and/or layers either in a plied-up configuration or in a bonded or otherwise attached form with one or more other layers of material. Thus, if the material of the present invention is being used to form the liquid permeable top sheet 12, it may be desirable to attach this layer to one or more of the other layers or components of the diaper 10 including, for example, the separation layer 22, the absorbent core 16 and/or bottom sheet 14. If the separation layer 22 is made from the material according to the present invention, it too may be attached to the liquid permeable top sheet and/or the absorbent core 16 and bottom sheet 14.

In order to function properly as a material according to the present invention, the fibrous nonwoven web must include certain properties which are maintained while under a compressive load. This is necessary so that, for example, when the material according to the present invention is incorporated into a diaper, it will function properly when placed under a compressive load such as is the case when a baby wearing the diaper is in a sitting position. To form a fibrous nonwoven web with the parameters outlined below, at least a portion of the fibers forming the web should be made from polymers which are heat bondable. By heat bondable, it is meant that the randomly deposited fibers forming the nonwoven web can be subjected to heat and/or ultrasonic energy of a sufficient degree that the fibers will adhere to one another at a plurality of the fiber crossover points due to the melting or partial softening of the polymer forming the heat bondable fibers. Suitable polymers for forming such heat bondable fibers are permanently fusible and are typically referred to as being thermoplastic. Examples of suitable thermoplastic polymers include, but are not limited to, polyolefins, polyesters, polyamides, orlon, acetates and poly vinyl alcohol as well as homopolymers, copolymers and blends of the foregoing. In addition, wetting agents/surfactants may be added either internally, such as with siloxane during the fiber formation process or externally as a post treatment either to the fibers and/or the resultant web as with anionic and nonionic surfactants including fluorocarbons. Such wetting agents/surfactants as well as their use are well-known and need not be described herein in detail.

The fibers formed from the aforementioned polymers may be short staple length fibers such as are used in the air laying and the bonded carded web processes or longer, more continuous fibers as are formed in, for example, the spunbonding process. Typical staple fiber lengths will range between about 38 and about 51 millimeters, though lengths outside this range also may be used. For example, air laying typically involves using fibers with lengths in the range of from about 6 to about 19 millimeters. Fibers having deniers between about 1.8 and about 32 and fiber diameters between about 10 and about 70 microns have been found to work particularly well with respect to the present invention.

In order to achieve the specified structure of the material of the present invention, it is desirable that the fibers be crimped. Crimping can be imparted both mechanically and/or chemically thereby forming both zig-zag or sawtooth and helically or spirally crimped fibers. Fiber cross-sections may be either circular or non-circular including, for example, bilobal, trilobal and X-shaped cross-sections. The fibers may be solid or hollow. In addition, they may be made from a single fiber polymer or from multiple polymers such as are found in multiconstitutent and multicomponent fibers collectively referred to as "multicomponent" fibers. Multiconstitutent fibers such as biconstitutent fibers tend to have two or more polymers which are present in or deposited throughout the fiber. Multicomponent fibers such as bicomponent fibers tend to have two or more polymers present in distinct and separate areas most typically along the longitudinal axis of the fiber. Thus, using bicomponent fibers as an example, fiber cross-sections may include, for example, sheath/core, side-by-side and islands-in-the-sea cross-sections. Typically with such fibers one of the polymers has a lower softening or melting point than the other polymer or polymers. This lower melting/softening polymer will often be present on at least a portion of the exterior or exposed surface of the fiber and is used to bond the fibers of the nonwoven web together.

The aforementioned fibers may be used in a number of processes to form the compressively resistant and resilient fibrous nonwoven web according to the present invention. Suitable processes will include those that yield a fibrous nonwoven web which has the range of physical properties described below. Suitable processes include, but are not limited to, air laying, spunbonding and bonded carded web formation processes. Spunbond nonwoven webs are made from fibers which are formed by extruding a molten thermoplastic material as filaments from a plurality of fine capillaries in a spinneret with the diameter of the extruded filaments then being rapidly reduced, for example, but non-eductive or eductive fluid drawing or other well-known spunbonding mechanisms. The production of spunbonded nonwoven webs is illustrated in patents such as Appel et al., U.S. Pat. No. 4,340,563, Dorschner et al., U.S. Pat. No. 3,692,618; McKinney, U.S. Pat. Nos. 3,338,992 and 3,341,394; Levy, U.S. Pat. No. 3,276,944; Peterson, U.S. Pat. No. 3,502,538; Hartmann, U.S. Pat. No. 3,502,763; Dobo et al., U.S. Pat. No. 3,542,615; Pike et al., U.S. Pat. No. 5,382,400; Matsuki et al., U.S. Pat. No. 3,802,871 and Harmon, Canadian Patent Number 803,714 which are all incorporated herein by reference in their entirety.

Bonded carded webs are made from staple fibers which are usually purchased in bales. The bales are placed in a picker which separates the fibers. Next, the fibers are sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powder adhesive is distributed through the web and is then activated by heating the web and adhesive with hot air. Another bonding method is pattern bonding wherein heated calendar rolls or ultrasonic bonding equipment is used to bond fibers together, usually in a localized bond pattern though the web can be bonded across its entire surface if so desired. The best mode though, when using bicomponent staple fibers is to use a through-air bonder which is well known in the art. In a through-air bonder, a flow of heated air is applied through the web to heat the web to a temperature above the melting or softening point of the lower melting component of the bicomponent fibers but below the melting or softening point of the higher melting component. Upon heating, the lower melting polymer portions of the web fibers are melted or softened and the melted/softened portions of the fibers adhere to adjacent fibers at the crossover points while the high melting polymer portions of the fibers tend to maintain the physical and dimensional integrity of the resultant nonwoven web. Typically the unbonded web is supported on a forming wire or drum. In addition, a vacuum may be pulled through the web if so desired to further contain the fibrous web during the bonding process.

Air laying is another well known process by which fibrous nonwoven webs according to the present invention can be made. In the air laying process, bundles of small fibers usually having lengths ranging between about 6 and 19 millimeters are separated and entrained in an air supply and then deposited onto a forming screen, oftentimes with the assistance of a vacuum supply. The randomly deposited fibers are then bonded to one another using, for example, hot air or a spray adhesive.

The fibrous nonwoven webs of the present invention can be made from a single type of fiber or a blend of fibers such as, for example, a blend of polyethylene single component fibers and one or more bicomponent fibers such as polyethylene sheath/polypropylene core or polyethylene sheath/polyester core bicomponent fibers.

The fibrous nonwoven web can be layered in either or both the X-Y plane and the Z-direction. If desired, it can also be joined to other layers and/or perforated to increase liquid strike through. For example, a blend of 50 weight percent 3 denier polyethylene sheath/polyester core and 50 weight percent 10 denier polyethylene sheath/polyester core fibers have been found to work well.

It is desirable that the compressively resistant and resilient fibrous nonwoven web according to the present invention be at least somewhat hydrophilic in order to aid in the transfer of liquid to the absorbent core 16. Some fibers are naturally hydrophilic. Other fibers such as polyolefins tend to be hydrophobic and therefore oftentimes require a surface treatment in order to increase their hydrophilicity. Triton X-102 surfactant from ICI Americas, Inc. of Wilmington, Del. is one example of a surfactant which can be used to increase the hydrophilicity of such a fibrous nonwoven web.

While it is desirable that the fibrous nonwoven web be somewhat hydrophilic, it is less desirable to increase the hydrophilicity to such an extent that the material tends to retain liquid and provide a wet contact surface for the skin of the wearer. Therefore, it may be necessary to adjust the degree of hydrophilicity up or down to meet this criterion.

Generally, the compressively resistant and resilient fibrous nonwoven web according to the present invention will comprise a plurality of randomly deposited fibers which are subsequently bonded, at least partially, to maintain the integrity and compression resistance of the web. Unlike a woven material which has a defined weaving pattern, fibrous nonwoven webs tend to have fibers that are randomly oriented with respect to one another. Bonded carded webs due to the carding process tend to have their fibers somewhat aligned in the machine direction, however, their fiber pattern is still random when compared to woven materials. In order to provide appropriate separation of an absorbent core from the wearer's skin, the fibrous nonwoven web according to the present invention should have a minimum thickness of 2.5 millimeters or greater when measured under a pressure of 68.9 pascals. The specific volume of the material is another important parameter. In a dry state, the specific volume of the fibrous nonwoven web according to the present invention should be 14 cubic centimeters per gram or greater at 6,895 pascals pressure. Both the foregoing parameters are measured as outlined below while the material is in a nonwetted state. The material of the present invention should also have a compression resistance of 25 percent or greater, a compression resiliency of 80% or greater, a Frazier air permeability of 100 cubic meters per square meter per minute, and a basis weight of at least about 50 grams per square meter whether in a single layer or multilayer configuration.

The material once made may be used in a wide variety of applications including, but not limited to, personal care absorbent products including, for example, diapers, training pants, incontinence devices, sanitary napkins, bandages and the like. Generally in such applications, the material of the present invention will be associated with the portion of the personal care absorbent product which is located on the side of the absorbent core which faces the wearer. Thus, it can be used as the liner or top sheet or it can be positioned between the liner and the absorbent core or it can form a portion of the liner or the core in the form of a composite which may or may not be laminated as, for example, by thermal or ultrasonic bonding, adhesives, needling, stitching and hydroentangling. It is also possible to use the material according to the present invention across the entire surface of the product or it can be used in select locations which may or may not be spaced apart from one another.

In order to define the various parameters outlined below with respect to the examples and claims, a series of tests are set forth for the purpose of measuring the herein-described parameters. In addition to the test procedures set forth below, a series of examples are also presented.

TEST PROCEDURES

FRAZIER AIR PERMEABILITY

The procedure used to determine Frazier air permeability was conducted in accordance with Federal Test Methods Standard No. 191A/5450. The specimen sizes should be at least 8 inches ×8 inches (20.3 cm ×20.3 cm). A larger size makes it possible to ensure that all sides of the specimen extended well beyond the retaining ring and facilitate clamping of the specimen securely and evenly across the orifice. Values were measured in cubic feet per square foot per minute ($ft^3/ft^2/min$). Values were multiplied by 0.305 to convert them to cubic meters per square meter per minute. A total of five samples were measured for each material and then averaged. The values reported are for the average.

BASIS WEIGHT

The basis weights for the samples were determined in accordance with Federal Test Method 191A/5041. Sample size was 5 inches by 5 inches (12.7 centimeters by 12.7 centimeters) and a total of 5 samples were weighed and then averaged for each material. The values reported are for the average.

SPECIFIC VOLUME, THICKNESS AND COMPRESSION RESISTANCE/RESILIENCY TEST

Specific volume, thickness, compression resistance and resiliency were measured using an INSTRON or SINTECH tensile tester to measures the resisting force as a material is compressed between a movable platen and a fixed base at a constant rate using a certain amount of force and subsequently releasing the force at the same rate. Preferably pressure, or force, and platen position are recorded. If only force is recorded, pressure is calculated using:

$$P_{reading} = \frac{F \cdot 10,000 \text{ cm}^2/\text{m}^2}{A_p}$$

where:

$P_{reading}$=pressure reading from the SINTECH or INSTRON in pascals
F=force pushing back on the platen in Newtons
$A_p$=area of the platen in square centimeters (19.02 cm$^2$)

Specific volume for a given platen position is calculated at a specific pressure (P) using the equation:

$$SV = \frac{(x_o - x) \cdot A_m \cdot 0.1 \text{ cm/mm}}{M}$$

where:

SV=specific volume of material in cubic centimeters per gram
$x_o$=distance of initial platen position from the base in millimeters
x=platen distance from initial position in millimeters at a specific pressure (P)
$A_m$=area of material in square centimeters
M=mass of material in grams for a surface area equal to that of the platen The base must be larger in size than the platen. Zero height between platen and base distance was set by bringing the platen down until it barely touches the base. The platen was then raised to the desired initial height from the zero distance. The initial platen position must be greater than the initial thickness of the material so that the test starts out at zero pressure on the sample. The material can be the same size as the platen or larger.

Suitable equipment for this test could include:
Compression tester:
INSTRON model 6021 with compression test software and 1 kN load cell made by Instron of Bucks, England.
Balance:
Mettler of Highstown, N.J., model PM4600
To measure thickness, the following equation was used:
Thickness=$x_o$-x where x is measured at 68.9 pascals
Thus all thickness values reported were for samples while under a load or pressure of 68.9 pascals.

For the purpose of measuring specific volume for the present specification, a 4.92 cm diameter circular platen was used to compress materials against the base at a rate of 5.00 mm/min up to a maximum load of 13.11 newtons. The platen was then returned at the same rate to the initial starting position. The initial starting position for the platen was 8 mm from the base. Material samples were cut to 5.04 cm diameter and tested in the center. Force and position data were recorded every 0.01 minutes or every 0.05 mm. Five repeats were performed on separate material pieces.

Wet specific volume was measured similarly to the dry specific volume except the sample was completely immersed in 0.9% saline throughout the test. A flat bottomed container such as a hexagonal polystyrene weighing dish catalog #02-202D from Fischer Scientific of Pittsburgh, Pa. was placed on the base and the platen was zeroed and set to the initial position as described in the dry specific volume method. The container bottom measured 9 cm across from flat side to flat side, not corner to corner. The open top for the same dimension measured 13 cm. The container was 3 centimeters deep. The container was filled with 0.09 percent saline to a level just above (approximately 1 millimeter) the bottom of the platen at its initial position. At this point in the procedure the load cell was tared. An appropriate saline could be S/P certified blood bank saline made by Stephens Scientific of Riverdale, N.J. and distributed by Baxter Healthcare of McGraw Park, Ill. under catalog #B3158-1. The load cell was tared with this level of fluid in the container. The sample was placed in the fluid, under the platen and the test was then performed as described above for the dry specific volume. Buoyant force was found to have a negligible effect (less than 68.9 pascals at maximum submersion) on pressure but if so desired it can be subtracted from the pressure readings at each platen position using the following equation:

$$P_B = D_{saline} \cdot g \cdot (x_o - x) \cdot \left| \frac{A_p}{A_d - A_p} + 1 \right| \cdot 0.01$$

where:

$P_B$=Pressure from buoyant force in pascals
$D_{saline}$=density in grams per cubic centimeter of 0.9% saline
$A_p$=area of the platen in square centimeters (18.9 cm$^2$)
$A_d$=area of the dish in square centimeters
$x_o$=initial platen position from the base in millimeters
x=platen position in millimeters
g=standard acceleration of gravity which is 981 cm/sec$^2$
0.01=conversion factor=0.1 cm/mm·0.001 kg/gm·100 cm/m The overall pressure on the sample becomes:
$P_{sample} = P_{reading} - P_B$
where:
$P_{sample}$=pressure on the sample from the platen in pascals
$P_{reading}$=pressure reading from the SINTECH or INSTRON in pascals
$P_B$=buoyancy pressure from the 0.9% saline in pascals For the purpose of measuring specific volume for the present specifications, 120 ml of saline was placed in the container and the platen was initially set 8.0 mm from the base.

Compression resiliency or percent recovery in either a wet or dry state at 68.9 pascals (0.01 psi) was calculated using the platen positions on compression and recovery when the pressure was 68.9 pascals:

$$\% \text{ Recovery} = \frac{SV_{recovery\ 68.9\ Pa}}{SV_{compression\ 68.9\ Pa}} \times 100\% \text{ or}$$

$$\frac{V_3}{V_1} \times 100\%$$

where:

$SV_{compression\ 68.9\ Pa}$=specific volume upon recovery at 68.9 pascals pressure, $V_3$
$SV_{compression\ 68.9\ Pa}$=specific volume upon compression at 68.9 pascals pressure, $V_1$ Both wet and dry compression resistance or percent resistance was calculated using the platen positions on compression when the pressure was 6895 pascals and compression when the pressure was 68.9 pascals:

$$\% \text{ Resistance} = \frac{SV_{compression\ 6895\ Pa}}{SV_{compression\ 68.9\ Pa}} \times 100\% \text{ or}$$

$$\frac{V_2}{V_1} \times 100\%$$

where:

$SV_{compression\ 6895\ Pa}$=specific volume upon compression at 6895 pascals pressure, $V_2$ $SV_{compression\ 68.9\ Pa}$=specific volume upon compression at 68.9 pascals pressure, $V_1$

EXAMPLES

EXAMPLE I

In Example I a through air bonded carded web was made using 10 denier (merge 1036) and 3 denier (merge 1053) polyethylene sheath/polyester core bicomponent staple fibers. Both of the fibers were manufactured by the BASF Corporation and had staple lengths of 51 and 38 millimeters respectively. The fibers were treated by the manufacturer with a surfactant to make them more hydrophilic. The two fibers were uniformly blended, carded and then through air bonded at a temperature of 133 degrees C. at a line speed of 15 meters per minute with a dwell time of 2.5 seconds. The resultant web had a respective 50/50 weight percent mixture of the two fibers based upon the total weight of the web and a basis weight of 152 grams per square meter. The specific volume values $V_1$, $V_2$ and $V_3$ were respectively 32.25, 17.06 and 28.72 cubic centimeters per gram. The compression resistance in all examples was calculated by dividing $V_2$ by $V_1$ and multiplying the result by 100 to yield percent. The compression resiliency or recovery in all examples was calculated by dividing $V_3$ by $V_1$ and multiplying the result by 100 to yield percent. The compression resistance of the web was 53 percent and the compression resiliency was 89 percent. In other words, when the sample was placed under a pressure or load of 6,895 pascals (1.0 pounds per square inch), the sample only compressed to 53 percent of its original thickness. Then upon release of the load, the sample recovered to 89 percent of its original thickness. Thickness was measured to be 4.90 millimeters and the Frazier air permeability was 154 cubic meters per square meter per minute.

EXAMPLE II

In Example II a through air bonded carded web was made using the same 10 denier and 3 denier polyethylene sheath/polyester core bicomponent staple fibers as were used in Example I. The two fibers were uniformly blended, carded and then through air bonded at a temperature of 133 degrees C. at a line speed of 15 meters per minute with a dwell time of 2.5 seconds. The resultant web had a respective 50/50 weight percent mixture of the two fibers (10 denier/3 denier) based upon the total weight of the web and a basis weight of 77 grams per square meter. The specific volume values $V_1$, $V_2$ and $V_3$ were respectively 40.43, 18.74 and 35.70 cubic centimeters per gram. The compression resistance of the web was 46 percent and the compression resiliency was 88 percent. Thickness was measured to be 3.11 millimeters and the Frazier air permeability was 285 cubic meters per square meter per minute.

The same material was also tested under wet conditions to show that materials of the present invention would behave similarly once they had been insulted by, for example, a baby in a diaper. The $V_{1wet}$, $V_{2wet}$ and $V_{3wet}$ specific volume values were respectively, 41.12, 18.27 and 35.86 cubic centimeters per gram. The wet compression resilience was 44 percent and the wet compression recovery was 87 percent. This is to be compared to dry values of 45 and 88 percent. Thus it can be seen that the respective changes between the wet and dry specific volume values were extremely low (0.69, –0.47 and 0.16) as were the changes in compression testing values thereby indicating that the wetting out of these materials will have little or no effect on their ability to maintain separation between, for example, a diaper liner and an absorbent core at the specified pressures. As a result, the materials of the present invention should be well-suited for use as a liner material or a separation material in between a liner material and an absorbent core of a personal care absorbent article.

EXAMPLE III

In Example III a through air bonded carded web was made using 10 denier (merge 1036) polyethylene sheath/polyester core bicomponent staple fibers manufactured by the BASF Corporation and 3 denier polyethylene sheath/polypropylene core bicomponent fibers designated ESC and manufactured by the Chisso Corporation of Osaka, Japan. The fibers had staple lengths of 51 and 38 millimeters respectively. The fibers were treated by the manufacturers with surfactants to make them more hydrophilic. The two fibers were uniformly blended, carded and then through air bonded at a temperature of 133 degrees C. at a line speed of 15 meters per minute with a dwell time of 2.5 seconds. The resultant web had a respective 70/30 weight percent mixture of the two fibers (10 denier/3 denier) based upon the total weight of the web and a basis weight of 75 grams per square meter. The specific volume values $V_1$, $V_2$ and $V_3$ were respectively 38.33, 17.08 and 33.58 cubic centimeters per gram. The compression resistance of the web was 45 percent and the compression resiliency was 88 percent. Thickness was measured to be 2.88 millimeters and the Frazier air permeability was 291 cubic meters per square meter per minute.

The material of Example III was also subjected to wet testing in the same fashion and under the same conditions as the material of Example II. Based upon the wet testing, the material of Example IV had wet specific volumes, $V_{1wet}$, $V_{2wet}$ and $V_{3wet}$, of 39.56, 17.59 and 34.52 cubic centimeters per gram. Here again as with Example II the difference between the wet and dry values was very small. In addition, the wet compression resiliency (44 percent) and the wet compression recovery (87 percent) were almost identical to their dry values (45 percent and 88 percent).

EXAMPLE IV

In Example IV a through air bonded carded web was made using 10 denier (merge 1036) polyethylene sheath/polyester core bicomponent staple fibers manufactured by the BASF Corporation and 1.5 denier rayon single component fibers designated 18453 and manufactured by Courtaulds North America, Inc. of New York, N.Y. The fibers had staple lengths of 51 and 38 millimeters respectively. The fibers were treated by the manufacturer with a surfactant to make them more hydrophilic. The two fibers were uniformly blended, carded and then through air bonded at a temperature of 133 degrees C. at a line speed of 15 meters per minute with a dwell time of 2.5 seconds. The resultant web had a respective 70/30 weight percent mixture of the two fibers (10 denier/1.5 denier) based upon the total weight of the web and a basis weight of 74 grams per square meter. The specific volume values $V_1$, $V_2$ and $V_3$ were respectively 27.53, 12.74 and 23.54 cubic centimeters per gram. The compression resistance of the web was 46 percent and the compression resiliency was 86 percent. Thickness was measured to be 2.16 millimeters and the Frazier air permeability was 256 cubic meters per square meter per minute. The material of this example only had a value $V_2$ of 12.74 compared to the requisite 14 cubic centimeters per gram. Thus it can be seen that the material of this example lacked the necessary specific volume while under a pressure of 6,895 pascals. As a result, a greater amount of fibrous nonwoven web material would have to be used to hold the same amount of liquid which is not cost effective.

EXAMPLE V

In Example V a through air bonded carded web was made using 10 denier (merge 1036) polyethylene sheath/polyester core bicomponent staple fibers manufactured by the BASF Corporation and 1.5 denier rayon single component fibers designated 18453 and manufactured by the Courtaulds North America, Inc. of New York, N.Y. The fibers had staple lengths of 51 and 38 millimeters respectively. The fibers were treated by the manufacturers with a surfactant to make them more hydrophilic. The two fibers were uniformly blended, carded and then through air bonded at a temperature of 133 degrees C. at a line speed of 15 meters per minute with a dwell time of 2.5 seconds. The resultant web had a respective 70/30 weight percent mixture of the two fibers (10 denier/1.5 denier) based upon the total weight of the web and a basis weight of 70 grams per square meter. The specific volume values $V_1$, $V_2$ and $V_3$ were respectively 25.90, 11.64 and 22.05 cubic centimeters per gram. The compression resistance of the web was 45 percent and the compression resiliency was 85 percent. Thickness was measured to be 1.81 millimeters and the Frazier air permeability was 243 cubic meters per square meter per minute. The material of this example only had a value $V_2$ of 11.64 compared to the requisite 14 cubic centimeters per gram. Thus it can be seen that the material of this example lacked the necessary specific volume while under a pressure of 6,895 pascals. As a result, a greater amount of fibrous nonwoven web material would have to be used to hold the same amount of liquid which is not cost effective.

EXAMPLE VI

In Example VI a through air bonded carded web was made using 3 denier polyethylene sheath/polyester core bicomponent staple fibers designated Type 256 and manufactured by the Hoechst Celanese Corporation of Salisbury, N.C. and 6 denier single component Type 295 polyester fibers also from the Hoechst Celanese Corporation. The fibers had staple lengths of 38 and 51 millimeters respectively. The fibers were treated by the manufacturer with a surfactant to make them more hydrophilic. The two fibers were uniformly blended, carded and then through air bonded at a temperature of 133 degrees C. at a line speed of 15 meters per minute with a dwell time of 2.5 seconds. The resultant web had a respective 60/40 weight percent mixture of the two fibers (3 denier/6 denier) based upon the total weight of the web and a basis weight of 133 grams per square meter. The specific volume values $V_1$, $V_2$ and $V_3$ were respectively 54.12, 10.65 and 42.38 cubic centimeters per gram. The compression resistance of the web was 20 percent and the compression resiliency was 78 percent. Thickness was measured to be 7.20 millimeters and the Frazier air permeability was 179 cubic meters per square meter per minute. The material of this example only had a value $V_2$ of 10.65 compared to the requisite 14 cubic centimeters per gram. Thus it can be seen that the material of this example lacked the necessary specific volume while under a pressure of 6,895 pascals. As a result, a greater amount of fibrous nonwoven web material would have to be used to hold the same amount of liquid which is not cost effective.

EXAMPLE VII

In Example VII a through air bonded carded web was made using 3 denier polyethylene sheath/polyester core bicomponent staple fibers designated Type 256 and manufactured by the Hoechst Celanese Corporation and 6 denier single component Type 295 polyester fibers also from the Hoechst Celanese Corporation. The fibers had staple lengths of 38 and 51 millimeters respectively. The fibers were treated by the manufacturer with a surfactant to make them more hydrophilic. The two fibers were uniformly blended, carded and then through air bonded at a temperature of 133 degrees C. at a line speed of 15 meters per minute with a dwell time of 2.5 seconds. The resultant web had a respective 60/40 weight percent mixture of the two fibers (3 denier/6 denier) based upon the total weight of the web and a basis weight of 62 grams per square meter. The specific volume values $V_1$, $V_2$ and $V_3$ were respectively 48.66, 11.96 and 39.21 cubic centimeters per gram. The compression resistance of the web was 25 percent and the compression resiliency was 81 percent. Thickness was measured to be 3.02 millimeters and the Frazier air permeability was 256 cubic meters per square meter per minute. The material of this example only had a value $V_2$ of 11.96 compared to the requisite 14 cubic centimeters per gram. Thus it can be seen that the material of this example lacked the necessary specific volume while under a pressure of 6,895 pascals. As a result, a greater amount of fibrous nonwoven web material would have to be used to hold the same amount of liquid which is not cost effective.

EXAMPLE VIII

In Example VIII a through air bonded carded web was made using 3 denier polyethylene sheath/polyester core bicomponent staple fibers designated Type 256 and manufactured by the Hoechst Celanese Corporation and 6 denier single component Type 295 polyester fibers also from the Hoechst Celanese Corporation. The fibers had staple lengths of 38 and 51 millimeters respectively. The fibers were treated by the manufacturer with a surfactant to make them more hydrophilic. The two fibers were uniformly blended, carded and then through air bonded at a temperature of 133 degrees C. at a line speed of 15 meters per minute with a dwell time of 2.5 seconds. The resultant web had a respective 60/40 weight percent mixture of the two fibers (3 denier/6 denier) based upon the total weight of the web and a basis weight of 64 grams per square meter. The specific volume values $V_1$, $V_2$ and $V_3$ were respectively 35.09, 10.68 and 28.35 cubic centimeters per gram. The compression resistance of the web was 31 percent and the compression resiliency was 81 percent. Thickness was measured to be 2.25 millimeters and the Frazier air permeability was 244 cubic meters per square meter per minute. The material of this example only had a value $V_2$ of 10.68 compared to the requisite 14 cubic centimeters per gram. Thus it can be seen that the material of this example lacked the necessary specific volume while under a pressure of 6,895 pascals. As a result, a greater amount of fibrous nonwoven web material would have to be used to hold the same amount of liquid which is not cost effective.

EXAMPLE IX

In Example IX a through air bonded carded web was made using the same 10 denier and 3 denier polyethylene sheath/polyester core bicomponent staple fibers as in Example I. The two fibers were uniformly blended, carded and then through air bonded at a temperature of 135 degrees C. at a line speed of 18.3 meters per minute with a dwell time of 2.08 seconds. The resultant web had a respective 50/50 weight percent mixture of the two fibers based upon the total weight of the web and a basis weight of 165 grams per square meter. The specific volume values $V_1$, $V_2$ and $V_3$ were respectively 38.4, 16.4 and 33.6 cubic centimeters per gram. The compression resistance of the web was 43 percent and the compression resiliency was 88 percent. Thickness was measured to be 6.33 millimeters and the Frazier air permeability was 151 cubic meters per square meter per minute.

EXAMPLE X

In Example X a through air bonded carded web was made using 10 denier (merge 1036) and polyethylene sheath/polyester core bicomponent staple fibers and 6 denier Type 429 polyethylene/polypropylene side-by-side bicomponent staple fibers. The 10 denier fibers were manufactured by the BASF Corporation and had a staple length of 51 millimeters. The 6 denier fibers were manufactured by the Hercules Corporation and had a staple length of 38 millimeters. Both the fibers were treated by the manufacturers with a surfactant to make them more hydrophilic. The two fibers were uniformly blended, carded and then through air bonded at a temperature of 143 degrees C. at a line speed of 23 meters per minute with a dwell time of 1.67 seconds. The resultant web had a respective 60/40 weight percent mixture of the two fibers based upon the total weight of the web and a basis weight of 55 grams per square meter. The specific volume values $V_1$, $V_2$ and $V_3$ were respectively 38.7. 18.4 and 33.1 cubic centimeters per gram. The compression resistance of the web was 48 percent and the compression resiliency was 86 percent. Thickness was measured to be 2.13 millimeters and the Frazier air permeability was 423 cubic meters per square meter per minute.

EXAMPLE XI

In Example XI a through air bonded carded web was made using 3 denier (merge 1053) polyethylene sheath/polyester core bicomponent staple fibers. The fibers were manufactured by the BASF Corporation and had a staple length of 38 millimeters. The fibers were treated by the manufacturer with a surfactant to make them more hydrophilic. The fibers were carded and then through air bonded at a temperature of 135 degrees C. at a line speed 18.3 meters per minute with a dwell time of 2.08 seconds. The resultant web had a basis weight of 154 grams per square meter. The specific volume values $V_1$, $V_2$ and $V_3$ were respectively 38.0, 17.7 and 30.2 cubic centimeters per gram. The compression resistance of the web was 47 percent and the compression resiliency was 91 percent. Thickness was measured to be 5.86 millimeters and the Frazier air permeability was 116 cubic meters per square meter per minute.

EXAMPLE XII

In Example XII a through air bonded carded web was made using the same 10 denier and 3 denier polyethylene sheath/polyester core bicomponent staple fibers as in Example I. The two fibers were uniformly blended, carded and then through air bonded at a temperature 135 degrees C. at a line speed of 18.3 meters per minute with a dwell time of 2.08 seconds. The resultant web had a respective 50/50 weight percent mixture of the two fibers based upon the total weight of the web and a basis weight of 161 grams per square meter. The specific volume values $V_1$, $V_2$ and $V_3$ were respectively 37.7, 16.4 and 32.4 cubic centimeters per gram. The compression resistance of the web was 43 percent and the compression resiliency was 88 percent. Thickness was measured to be 6.40 millimeters and the Frazier air permeability was 148 cubic meters per square meter per minute.

EXAMPLE XIII

In Example XIII a through air bonded carded web was made using 10 denier (merge 1036) polyethylene sheath/polyester core bicomponent staple fibers. The fibers were manufactured by the BASF Corporation and had a staple length of 51 millimeters. The fibers were treated by the manufacturer with a surfactant to make them more hydrophilic. The fibers were carded and then through air bonded at a temperature of 138 degrees C. at a line speed of 18.3 meters per minute with a dwell time of 2.08 seconds. The resultant web had a basis weight of 186 grams per square meter. The specific volume values $V_1$, $V_2$ and $V_3$ were respectively 30.3, 17.0 and 27.3 cubic centimeters per gram. The compression resistance of the web was 56 percent and the compression resiliency was 90 percent. Thickness was measured to be 5.63 millimeters and the Frazier air permeability was 201 cubic meters per square meter per minute.

EXAMPLE XIV

In Example XIV a through air bonded carded web was made using the same 10 denier and 3 denier polyethylene sheath/polyester core bicomponent staple fibers as in Example I. The two fibers were uniformly blended, carded and then through air bonded at a temperature of 135 degrees C. at a line speed of 18.3 meters per minute with a dwell time of 2.08 seconds. The resultant web had a 50/50 weight percent mixture of the two fibers based upon the total weight of the web and a basis weight of 174 grams per square meter. The specific volume values $V_1$, $V_2$ and $V_3$ were respectively 34.1, 16.6 and 30.7 cubic centimeters per gram. The compression resistance of the web was 49 percent and the compression resiliency was 90 percent. Thickness was measured to be 5.92 millimeters and the Frazier air permeability was 141 cubic meters per square meter per minute.

EXAMPLE XV

In Example XV a through air bonded carded web was made using 10 denier (merge 1036) polyethylene sheath/polyester core bicomponent staple fibers manufactured by the BASF Corporation and 6 denier Type 429 polyethylene/polypropylene side-by side bicomponent fibers manufactured by the Hercules Corporation. Both of the fibers were treated by the manufacturers with a surfactant to make them more hydrophilic. The 10 denier fibers had a staple length of 51 millimeters and the 6 denier fibers had a staple length of 38 millimeters. The two fibers were uniformly blended, carded and then through air bonded at a temperature of 135 degrees C. at a line speed of 18.3 meters per minute with a dwell time of 2.08 seconds. The resultant web has a 50/50 weight percent mixture of the two fibers based upon the total weight of the web and a basis weight of 244 grams per square meter. The specific volume values $V_1$, $V_2$ and $V_3$ were respectively 24.6, 16.2 and 23.0 cubic centimeters per gram. The compression resistance of the web was 68 percent and the compression resiliency was 96 percent. Thickness was measured to be 6.01 millimeters and the Frazier air permeability was 128 cubic meters per square meter per minute.

EXAMPLE XVI

In Example XVI a through air bonded carded web was made using 10 denier (merge 1036) polyethylene sheath/polyester core bicomponent staple fibers and 9 denier Type 205 polyester staple fibers. The first fibers were manufactured by the BASF Corporation. The second fibers were manufactured by the Hoechst Celanese Corporation. Both had a staple length of 51 millimeters. Both fibers were treated by the respective manufacturers with a surfactant to make them more hydrophilic. The two fibers were uniformly blended, carded and then through air bonded at a temperature of 143 degrees C. at a line speed of 23 meters per minute with a dwell time of 1.67 seconds. The resultant web had a respective 60/40 weight percent mixture of the two fibers based upon the total weight of the web and a basis weight of 56 grams per square meter. The specific volume values $V_1$, $V_2$ and $V_3$ were respectively 78.4, 15.0 and 56.4 cubic centimeters per gram. The compression resistance of the web was 19 percent and the compression resiliency was 72 percent. Thickness was measured to be 4.40 millimeters and the Frazier air permeability was in excess of 518 cubic meters per square meter per minute. The material of this example only had a compression resistance of 19 percent as compared to the requisite 25 percent. Thus it can be seem that the material of this example lacked the necessary resistance to compression that would be necessary in such applications as a personal care absorbent article. Without the necessary compression resistance, the product body side liner would be more prone to rewet by liquid already absorbed and contained within the absorbent core.

EXAMPLE XVII

In Example XVII a through air bonded carded web was made using 1.8 denier (merge 1043) polyethylene sheath/polyester core bicomponent staple fibers and 6 denier Type 429 polyethylene/polypropylene side-by-side bicomponent staple fibers. The 1.8 denier fibers were manufactured by the BASF Corporation. The 6 denier fibers were manufactured by the Hercules Corporation. Each had a staple length of 38 millimeters. Both fibers were treated by the respective manufacturers with a surfactant to make them more hydrophilic. The two fibers were uniformly blended, carded and then through air bonded at a temperature of 143 degrees C. at a line speed of 23 meters per minute with a dwell time of 1.67 seconds. The resultant web had a respective 60/40 weight percent mixture of the two fibers based upon the total weight of the web and a basis weight of 50 grams per square meter. The specific volume values $V_1$, $V_2$ and $V_3$ were respectively 29.1, 14.6 and 25.2 cubic centimeters per gram. The compression resistance of the web was 50 percent and the compression resiliency was 87 percent. Thickness was measured to be 1.44 millimeters and the Frazier air permeability was 232 cubic meters per square meter per minute. As a result, this material lacked the necessary separation required for such products.

EXAMPLE XVIII

In Example XVIII a through air bonded carded web was made using 3 denier (merge 1053) polyethylene sheath/polyester core bicomponent staple fibers and 16 denier Type 295 polyester staple fibers. The 3 denier fibers were manufactured by the BASF Corporation and had a staple length of 38 millimeters. The 16 denier fibers were manufactured by the Hoechst Celanese Corporation and had a staple length of 51 millimeters. The fibers were treated by the respective manufacturers with surfactants to make them more hydrophilic. The two fibers were uniformly blended, carded and then through air bonded at a temperature of 143 degrees C. at a line speed of 23 meters per minute with a dwell time of 1.67 seconds. The resultant web had a respective 60/40 weight percent mixture of the two fibers based upon the total weight of the web and a basis weight of 42 grams per square meter. The specific volume values $V_1$, $V_2$ and $V_3$ were respectively 61.3, 14.1 and 49.1 cubic centimeters per gram. The compression resistance of the web was 23 percent and the compression resiliency was 80 percent. Thickness was measured to be 2.56 millimeters and the Frazier air permeability was 434 cubic meters per square meter per minute. Due to the low compression resistance, this material would still have problems with rewet from the absorbent core. This problem would persist even if plied in multiple layers.

EXAMPLE XIX

In Example XIX a comparative polyurethane reticulated foam sample was evaluated. The reticulated foam had 10 pores per inch (3.94 pores per centimeter) and was manufactured by the Federal Foam Company of New Richmond, Wis. and sold under the trade designation 80,000. The foam sample had a basis weight of 184 grams per square meter, a thickness of 5.94 millimeters at 68.9 pascals pressure and a Frazier air permeability in excess of 518 cubic meters per square meter per minute. It had specific volume values $V_1$, $V_2$ and $V_3$ of 32.4, 13.6 and 31.1 cubic centimeters per gram. The compression resistance was 42 percent and the compression resiliency or recovery was 96 percent. Hereagain it can be seen that the specific volume at 6,895 pascals was too low for the present invention. The material could serve as a separation layer, however, when placed in a product and placed under a pressure greater than 3448 pascals, it would collapse. Consequently, it would take more of the material to provide a desired level of separation while under load.

Based upon the foregoing examples, it can be seen that there are many parameters which come into play in designing a compressively resistant and resilient fibrous nonwoven web which will perform adequately in, for example, personal care absorbent articles. The materials of the present invention provide a means for adequately separating the body side liner from the absorbent core in a manner that is cost effective without undue bulking of the resultant product.

Having thus described the invention in detail, it should be apparent that various modifications and changes can be made in the present invention without departing from the spirit and scope of the following claims.

We claim:

1. A compressively resistant and resilient fibrous nonwoven web comprising:

a plurality of randomly-deposited fibers bonded to one another to form a nonwoven web, said nonwoven web having a thickness of 2.5 millimeters or greater at a pressure of 68.9 pascals, a specific volume of 14 cubic centimeters per gram or greater at a pressure of 6,895 pascals, a compression resistance of 25 percent or greater and a compression resiliency of 80 percent or greater.

2. The nonwoven web of claim 1 which has a Frazier air permeability of 100 cubic meters per square meter per minute or greater.

3. The nonwoven web of claim 1 wherein at least a portion of said plurality of fibers are bicomponent fibers.

4. The nonwoven web of claim 3 wherein said plurality of fibers are thermally bonded.

5. A personal care absorbent product comprising:

a liquid-permeable top sheet and a bottom sheet with an absorbent core disposed therebetween, said top sheet comprising the nonwoven web of claim 1.

6. The personal care absorbent product of claim 5 wherein said product is a diaper.

7. The personal care absorbent product of claim 5 wherein said product is a training pant.

8. The personal care absorbent product of claim 5 wherein said product is an incontinence device.

9. The personal care absorbent product of claim 5 wherein said product is a sanitary napkin.

10. The personal care absorbent product of claim 5 wherein said product is a bandage.

11. A compressively resistant and resilient fibrous nonwoven web comprising:

a plurality of fibers thermally bonded to form a nonwoven web wherein at least a portion of said fibers comprise bicomponent fibers, said nonwoven web having a thickness of 2.5 millimeters or greater at a pressure of 68.9 pascals, a specific volume of 14 cubic centimeters per gram or greater at a pressure of 6,895 pascals, a compression resistance of 25 percent or greater, a compression resiliency of 80 percent or greater and a Frazier air permeability of 100 cubic meters or greater.

12. The nonwoven web of claim 11 wherein at least a portion of said plurality of fibers are bicomponent fibers.

13. The nonwoven web of claim 12 wherein said plurality of fibers are thermally bonded.

14. A personal care absorbent product comprising:

a liquid-permeable top sheet and a bottom sheet with an absorbent core disposed therebetween, said top sheet comprising the nonwoven web of claim 11.

15. The personal care absorbent product of claim 14 wherein said product is a diaper.

16. The personal care absorbent product of claim 14 wherein said product is a training pant.

17. The personal care absorbent product of claim 14 wherein said product is an incontinence device.

18. The personal care absorbent product of claim 14 wherein said product is a sanitary napkin.

19. The personal care absorbent product of claim 14 wherein said product is a bandage.

20. A personal care absorbent product comprising:

a liquid-permeable top sheet and a bottom sheet with an absorbent core disposed therebetween and a separation layer disposed between said top sheet and said absorbent core, said separation layer comprising the nonwoven web of claim 1.

21. The personal care absorbent product of claim 20 wherein said product is a diaper.

22. The personal care absorbent product of claim 20 wherein said product is a training pant.

23. The personal care absorbent product of claim 20 wherein said product is an incontinence device.

24. The personal care absorbent product of claim 20 wherein said product is a sanitary napkin.

25. The personal care absorbent product of claim 20 wherein said product is a bandage.

26. A personal care absorbent product comprising:

a liquid-permeable top sheet and a bottom sheet with an absorbent core disposed therebetween and a separation layer disposed between said top sheet and said absorbent core, said separation layer comprising the nonwoven web of claim 11.

27. The personal care absorbent product of claim 26 wherein said product is a diaper.

28. The personal care absorbent product of claim 26 wherein said product is a training pant.

29. The personal care absorbent product of claim 26 wherein said product is an incontinence device.

30. The personal care absorbent product of claim 26 wherein said product is a sanitary napkin.

31. The personal care absorbent product of claim 26 wherein said product is a bandage.

* * * * *